US008969502B2

(12) United States Patent
Knott et al.

(10) Patent No.: US 8,969,502 B2
(45) Date of Patent: Mar. 3, 2015

(54) PROCESS FOR PREPARING POLYDIMETHYLSILOXANES ON SULPHONIC ACID CATION EXCHANGE RESINS

(71) Applicant: Evonik Goldschmidt GmbH, Essen (DE)

(72) Inventors: Wilfried Knott, Essen (DE); Martin Glos, Borken (DE); Norbert Nilewski, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/097,303

(22) Filed: Dec. 5, 2013

(65) Prior Publication Data
US 2014/0094532 A1 Apr. 3, 2014

Related U.S. Application Data

(62) Division of application No. 12/744,271, filed as application No. PCT/EP2008/062603 on Sep. 22, 2008, now Pat. No. 8,609,798.

(30) Foreign Application Priority Data

Nov. 21, 2007 (DE) .......................... 10 2007 055 484

(51) Int. Cl.
| *C08G 77/08* | (2006.01) |
| *C08J 9/00* | (2006.01) |
| *C07F 7/08* | (2006.01) |
| *C08G 18/40* | (2006.01) |
| *C08G 18/65* | (2006.01) |
| *C08G 77/04* | (2006.01) |
| *C08G 77/10* | (2006.01) |
| *C08L 83/04* | (2006.01) |
| *C08G 77/06* | (2006.01) |
| *C08G 101/00* | (2006.01) |

(52) U.S. Cl.
CPC ............. *C08J 9/0042* (2013.01); *C07F 7/0849* (2013.01); *C07F 7/0874* (2013.01); *C08G 18/4072* (2013.01); *C08G 18/6594* (2013.01); *C08G 77/045* (2013.01); *C08G 77/08* (2013.01); *C08G 77/10* (2013.01); *C08L 83/04* (2013.01); *C08G 77/06* (2013.01); *C08G 2101/0008* (2013.01); *C08G 2101/0083* (2013.01)
USPC .................. 528/23; 528/10; 521/91; 556/456

(58) Field of Classification Search
USPC ........................... 528/10, 23; 556/456; 521/91
See application file for complete search history.

(56) References Cited

U.S. PATENT DOCUMENTS

| 3,694,405 | A | | 9/1972 | Litteral | |
|---|---|---|---|---|---|
| 4,593,114 | A | * | 6/1986 | Lewis et al. | 556/450 |
| 5,273,670 | A | * | 12/1993 | Endres et al. | 508/208 |
| 5,430,166 | A | | 7/1995 | Klein et al. | |
| 5,455,367 | A | | 10/1995 | Klein et al. | |
| 5,475,127 | A | | 12/1995 | Klein et al. | |
| 5,563,229 | A | * | 10/1996 | Kawamoto et al. | 528/21 |
| 5,773,403 | A | * | 6/1998 | Hijino et al. | 510/411 |
| 6,291,622 | B1 | | 9/2001 | Drose et al. | |
| 6,307,082 | B1 | | 10/2001 | Klein et al. | |
| 6,858,663 | B2 | | 2/2005 | Knott et al. | |
| 7,018,458 | B2 | | 3/2006 | Knott et al. | |
| 7,125,585 | B2 | | 10/2006 | Dudzik et al. | |
| 7,157,541 | B2 | | 1/2007 | Knott et al. | |
| 7,196,153 | B2 | | 3/2007 | Burkhart et al. | |
| 7,598,334 | B2 | | 10/2009 | Ferenz et al. | |
| 7,612,158 | B2 | | 11/2009 | Burkhart et al. | |
| 7,612,159 | B2 | | 11/2009 | Burkhart et al. | |
| 7,619,035 | B2 | | 11/2009 | Henning et al. | |
| 7,645,848 | B2 | | 1/2010 | Knott et al. | |
| 7,754,778 | B2 | | 7/2010 | Knott et al. | |
| 2003/0224925 | A1 | | 12/2003 | Nakayama et al. | |
| 2004/0147703 | A1 | | 7/2004 | Burkhart et al. | |
| 2004/0214931 | A1 | * | 10/2004 | Ihara et al. | 524/265 |
| 2006/0293481 | A1 | | 12/2006 | Seelye et al. | |
| 2007/0128143 | A1 | | 6/2007 | Gruning et al. | |
| 2008/0146688 | A1 | | 6/2008 | Glos et al. | |
| 2008/0153934 | A1 | | 6/2008 | Neumann et al. | |
| 2008/0153992 | A1 | | 6/2008 | Knott et al. | |
| 2008/0153995 | A1 | | 6/2008 | Knott et al. | |
| 2009/0088488 | A1 | | 4/2009 | Bruckner et al. | |
| 2009/0137751 | A1 | | 5/2009 | Knott et al. | |
| 2009/0137752 | A1 | | 5/2009 | Knott et al. | |
| 2010/0022435 | A1 | | 1/2010 | Henning et al. | |

(Continued)

FOREIGN PATENT DOCUMENTS

DE 2511475 9/1975
DE 60305788 T2 6/2007

(Continued)

OTHER PUBLICATIONS

Cazacu M. et al., "Dimethyldiphenylsiloxane Copolymers Synthesis by Ion Exchanger Catalysis", Polymer 38 (15):3967-3971 (Jul. 1997).

(Continued)

*Primary Examiner* — Margaret Moore
(74) *Attorney, Agent, or Firm* — Scully, Scott, Murphy & Presser, P.C.

(57) ABSTRACT

The invention relates to a process for the targeted reorganization of polydimethylsiloxanes over sulphonic acid-containing cation exchange resins which have water contents of 8 to 25% by weight, and polydimethylsiloxanes thus prepared and the use thereof.

8 Claims, No Drawings

(56) References Cited

U.S. PATENT DOCUMENTS

| | | |
|---|---|---|
| 2010/0029587 A1 | 2/2010 | Bruckner et al. |
| 2010/0041910 A1 | 2/2010 | Schubert et al. |
| 2010/0056649 A1 | 3/2010 | Henning et al. |
| 2010/0071849 A1 | 3/2010 | Knott et al. |
| 2010/0081781 A1 | 4/2010 | Schubert et al. |
| 2010/0105843 A1 | 4/2010 | Knott et al. |
| 2010/0113633 A1 | 5/2010 | Henning et al. |
| 2010/0168367 A1 | 7/2010 | Schubert et al. |
| 2010/0292357 A1 | 11/2010 | Knott et al. |
| 2012/0027712 A1* | 2/2012 | Teshigawara et al. ..... 424/70.31 |

FOREIGN PATENT DOCUMENTS

| | | |
|---|---|---|
| EP | 1439200 A1 | 7/2004 |
| WO | 2007002344 A2 | 1/2007 |
| WO | 2009065641 A1 | 5/2009 |
| WO | 2009065644 A1 | 5/2009 |

OTHER PUBLICATIONS

International Search Report dated Mar. 30, 2009 received from the European Patent Office from related International Application No. PCT/EP2008/062603.

United States Official Action dated Mar. 19, 2013 from related U.S. Appl. No. 12/744,271.

United States Final Official Action dated Nov. 15, 2012 from related U.S. Appl. No. 12/744,271.

United States Official Action dated Jul. 31, 2012 from related U.S. Appl. No. 12/744,271.

* cited by examiner

PROCESS FOR PREPARING POLYDIMETHYLSILOXANES ON SULPHONIC ACID CATION EXCHANGE RESINS

CROSS REFERENCE TO RELATED APPLICATIONS

This application is a divisional of U.S. application Ser. No. 12/744,271, filed May 21, 2010, which is a 371 of International Application having Serial No. PCT/EP2008/062603, filed Sep. 22, 2008, which claims priority of German Patent Application No. 10 2007 055 484.4, filed Nov. 21, 2007, which are incorporated herein by reference in their entirety.

The invention relates to a process for the reorganization of polydimethylsiloxanes over sulphonic acid-containing cation exchange resins which have water contents of 8 to 25% by weight, and polydimethylsiloxanes thus prepared and the use thereof. Reorganization is understood as meaning the rearrangement of the siloxane bonds in polydimethylsiloxanes.

Low molecular weight polysiloxanes, in particular polydimethylsiloxanes, have become very important as cell-regulating stabilizers in polyurethane foams, in particular polyurethane foams of the so-called cold foam type (high resilience PU foams, HR polyurethane foams). In principle, the typical cold foam stabilizers are polymers based on polysiloxanes which are modified to greater or lesser extent by suitable organic groups. In intrinsically stable systems, unmodified polydimethylsiloxanes of the formula (I)

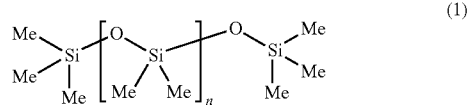

are preferably used, the total number of Si atoms may be $N=n+2$, where n may be $\geq 1$.

Industrially, these polydimethylsiloxanes are obtained by the reorganization/equilibration of siloxane cycles (such as, for example, $D_3/D_4/D_5$) or longer-chain polydimethylsiloxanes with hexamethyldisiloxane over acidic catalysts. Acidic catalysts used are, for example, acid-activated bleaching earths (bentonites, montmorillonites, Fuller's earths, etc.) and sulphonic acid-containing, macrocrosslinked cation exchange resins.

Thus, U.S. Pat. No. 3,694,405, which is hereby incorporated in its entirety also with respect to the present invention, describes the reorganization/equilibration of organosiloxanes over macroreticular, sulphonic acid-containing cation exchange resins having a mean pore volume of at least 0.01 cm³/g. AMBERLYST 15 is used in Example 2 as a typical member of these catalysts. At a reaction temperature of 41° C. and residence times of 10 to 60 minutes, mixtures of siloxane cycles and hexamethyldisiloxane react over this acidic solid phase to give equilibrates which have a relatively small proportion of polydimethylsiloxanes having chain lengths of $N=3, 4, 5, 6$ or 7, which are present in each case only in proportions of 3 to 4% by weight, but a high proportion of high molecular weight oligomers (chain length $N>7$) of 72.0 to 72.5% by weight. The catalysts used in U.S. Pat. No. 3,694,405 have, according to the working examples, water contents of <1% by weight.

DE 103 01 355 (US 2004147703), which is hereby incorporated in its entirety also with respect to the present invention, describes a process for the preparation of equilibration products of organosiloxanes by rearrangement of the siloxane bond over a cation exchange resin, in which an organosiloxane used as starting material or an organosiloxane mixture is brought into contact at a temperature of 10° C. to 120° C. with a macrocrosslinked cation exchange resin containing sulphonic acid groups and equilibrated organosiloxanes obtained are isolated, which is characterized in that a cation exchange resin whose product P of specific surface area and mean pore diameter is $P \geq 2.2 \times 10^{-3}$ m³/kg and whose specific surface area A is $\geq 35$ m²/g is used. A dried cation exchange resin or cation exchange resin having a water content of 5% by weight is used.

In relation to the equilibration of polydimethylsiloxanes over sulphonic acid-containing resins and the subsequent reactivation thereof by treatment with low molecular weight siloxanes, EP 1 367 079 (US 2003224925) refers to the importance of the water content of the sulphonic acid-containing cation exchange resin and indicates that a water load of <7, preferably 5, percent by mass should be established in order to obtain optimum polymerization conditions.

The behaviour during use of polydimethylsiloxane compositions as HR polyurethane foam stabilizers is very greatly dependent on the chain length of the polydimethylsiloxanes present in the composition and relative ratios thereof. Particularly suitable as HR polyurethane foam stabilizers are those polydimethylsiloxane compositions which have a high proportion of oligomers having a chain length N of 6 to 12 or preferably consist exclusively of these. In order to separate such particularly suitable compositions of equilibrates, as can be obtained, for example, according to the teaching of U.S. Pat. No. 3,694,405, considerable separation effort is necessary.

DE-A-25 33 074 describes a process for the preparation of cold foams using, inter alia, polydimethylsiloxanes of the general formula (1), which is characterized in that polydimethylsiloxanes used are those in which $N=(n+2)=4$ to 12, the total content of polydimethylsiloxanes with N equals 13 to 22 not being permitted to exceed 0.5% and it being necessary completely to separate off species with $N>22$. Here, reference is made to the fact that it is very important to pay attention to the chain length distribution.

In EP 1 095 968, good foam stabilization power is confirmed for the proposed solution based on DE 25 33 074, but the poor dimension stability is criticized. For eliminating this disadvantage, it is proposed to increase the proportions of polydimethylsiloxanes with N from 7 to 9 to at least 90% by weight of the siloxane mixture. In order to achieve this, distillation columns having a demanding design are used. By means of this time-consuming, energy-intensive and a hence expensive preparation process, the desired products can be provided.

It was therefore an object of the present invention to provide a process for the preparation of polysiloxanes, in particular polydimethylsiloxane compositions, which are suitable as HR polyurethane foam stabilizers, which process avoids one or more of the disadvantages of the processes of the prior art. In particular, it was intended to provide a process for the preparation of those suitable polydimethylsiloxanes which manage without a complicated thermal separation step.

Surprisingly, it has now been found that polydimethylsiloxanes can be obtained in a composition directly suitable for use as HR polyurethane foam stabilizers if the reorganization thereof is carried out over a sulphonic acid-containing cation exchange resin which has a water content of 8 to 25% by weight.

The present invention also relates to polydimethylsiloxane compositions obtainable by the process according to the invention, and the use of the compositions as PU cold foam stabilizers.

The polydimethylsiloxane compositions obtainable by the process according to the invention surprisingly already have such small amounts of relatively high molecular weight fractions which may interfere during the foaming that it is possible to dispense with separating off the substances by a distillation.

The process according to the invention therefore has the advantage that a polydimethylsiloxane composition which can be used directly as a stabilizer in polyurethane foams without it being necessary to carry out a complicated, expensive separation process is obtained directly by the reorganization. By means of the process according to the invention, in particular a substantial increase in the selectivity with respect to the desired products which can be used in the preparation of HR polyurethane foams is achieved.

For the special case where any small amounts of relatively high molecular weight polydimethylsiloxanes present or any low-boiling siloxanes present in the composition obtained by the process according to the invention were to present problems in certain applications, these compounds can be removed from the composition by a simple distillation.

The polydimethylsiloxane compositions according to the invention, the use thereof in PU-HR foam and the process for their preparation are described below by way of example without it intended to limit the invention to these being exemplary embodiments. When ranges, general formulae or classes of compounds are stated below, these are not intended to comprise only the corresponding ranges or groups of compounds which are specifically mentioned but also all part-ranges and part-groups of compounds which can be obtained by removal of individual values (ranges) or compounds. If documents are cited in the present description, the content thereof is intended to belong completely to the disclosure content of the present invention.

The process according to the invention for the preparation of polydimethylsiloxanes by reorganization of polydimethylsiloxanes over sulphonic acid-containing cation exchange resins is distinguished in that cation exchange resins, in particular sulphonic acid-containing cation exchange resins, which have 8 to 25% by weight, preferably 10 to 20% by weight, particularly preferably 12 to 18% by weight, of water are used. The water content can be determined on the basis of the method of the determination according to Karl Fischer, as described in DIN 51777, DGF E-III 10 and DGF C-III 13a.

The sulphonic acid-containing cation exchange resin used according to the invention and having water contents in said ranges can be prepared, starting from cation exchange resins having higher water contents, by physical and/or chemical drying. The physical drying can be effected, for example, in a drying oven, preferably at temperatures of 40 to 100° C., it being possible also to employ reduced pressure or to apply an inert gas stream for supporting the drying. Progress of the drying can be observed and controlled by a regular water determination. Alternatively, the sulphonic acid-containing cation exchange resins used according to the invention can also be chemically dried by bringing them into contact with siloxanes of low molecular weight, as described, for example, in EP 1 367 079.

The preparation of sulphonic acid-containing cation exchange resins used according to the invention and having water contents of 8 to 25% by weight can optionally also start from cation exchange resins of reduced water content. For this purpose, the cation exchange resin is brought into contact with water. In the simplest case, it is sufficient to store the sulphonic acid-containing resin over a defined period in the usual atmosphere so that its intrinsic hygroscopicity leads to an increased water load.

If the sulphonic acid-containing cation exchange resin defined with respect to its water content is used for the reorganization of polydimethylsiloxanes, it may be advantageous to add to the reactant system defined amounts of water, in particular to effectively counteract the decrease in water content of the resin—in particular below the limit according to the invention of 8% by weight of water—caused by interactions with other components of the reactant system. The metering in can be effected continuously or batchwise. Any necessary addition of water can be determined by determination of the water present in the reaction discharge or alternatively by (regular) determination of the water content in the cation exchange resin.

Cation exchange resins which may be used are in principle all sulphonic acid-containing cation exchange resins. Suitable cation exchange resins are, for example, those which are prepared by sulphonation of phenol/aldehyde condensates or of cooligomers of aromatic vinyl compounds. Examples of aromatic vinyl compounds for the preparation of the cooligomers are: styrene, vinyltoluene, vinylnaphthalene, vinylethylbenzene, methylstyrene, vinylchlorobenzene, vinylxylene and divinylbenzene. In particular, the cooligomers which form by reaction of styrene with divinylbenzene are used as a precursor for the preparation of cation exchange resins having sulphonic acid groups. The resins can be prepared in principle to be gel-like, macroporous or sponge-like. The properties of these resins, in particular specific surface area, porosity, stability, swelling or shrinkage and exchange capacity, can be varied by the preparation process. Instead of gelatinous sulphonic acid-containing cation exchange resins, porous, preferably macroporous, sulphonic acid-containing cation exchange resins are preferably used.

In the process according to the invention, customary commercially available macroporous sulphonic acid-containing cation exchange resins, such as, for example, Purolite® C 145, Purolite® C 150 MBH, Lewatit® K 2621, Lewatit® K 2629 or Lewatit® SP 121, can preferably be used in their acidic, so-called "H form". Among the suitable polymer phases of the styrene-divinylbenzene type which are commercially available, a preferred cation exchange resin here is one whose product P of specific surface area and mean pore diameter is $P \geq 2.2 \times 10^{-3}$ m$^3$/kg and whose specific surface area A is $\geq 35$ m$^2$/g. A cation exchange resin whose average specific surface area is in the range from 35 to 50 m$^2$/g is preferably used. Lewatit® K 2621 (Bayer AG) is particularly preferably used as sulphonic acid-containing cation exchange resin.

In addition to the use of fresh cation exchange resin as catalyst, it is however also possible to use a sulphonic acid-containing resin already used by the process according to the invention for the reorganization of polydimethylsiloxane compositions. Small residual amounts of reorganized product which may then adhere to the surface of the catalyst usually do not present problems.

All customary straight-chain and/or cyclic siloxanes can be used as siloxane raw materials in the process according to the invention. Mixtures which comprise low molecular weight linear dimethylsiloxanes together with cyclic siloxanes and hexamethyldisiloxane as a chain terminator are preferably reorganized. The upper limit of the viscosity of the polydimethylsiloxanes used here should preferably be not more than 500 mPa·s. The chain length of the siloxanes used is preferably in the range from 2 to 200 Si atoms.

Mixtures comprising or consisting of hexamethyldisiloxane and/or octamethyltrisiloxane and siloxane cycles, such as, for example, hexamethylcyclotrisiloxane ($D_3$), octamethylcyclotetrasiloxane ($D_4$) and/or decamethylcyclopentasiloxane ($D_5$), can preferably be used as siloxane raw materials. Industrial mixtures containing or preferably consisting of hexamethyldisiloxane and $D_4$ and $D_5$ are preferably used.

The reorganization is preferably carried out at a temperature of 10° C. to 110° C., preferably at a temperature of 25° C. to 100° C. The reorganization can optionally be carried out at reduced pressure, atmospheric pressure or superatmospheric pressure. Here, atmospheric pressure is to be understood as meaning, in addition to the definition introduced, the respective prevailing air pressure of the surrounding atmosphere. The reorganization is preferably carried out at a pressure of 950 mbar to 1100 mbar, particularly preferably at 1013 mbar.

It may be advantageous to carry out the reorganization in reaction times of 20 minutes to 7 hours, preferably in 30 minutes to 5 hours. By maintaining said reaction times, high selectivity with respect to polydimethylsiloxanes having chain lengths of $N=6$ to $N=12$ in the range of 20 to 58% by mass can be achieved.

Very particularly preferably, the reorganization is carried out at a temperature of 25° C. to 100° C., a pressure of about 1013±10 mbar and in a period of 30 minutes to 5 hours.

If desired, the reorganization can also be carried out in the presence of a solvent. Suitable solvents are all those solvents which are inert to cation exchange resin (catalyst) starting materials and products during the reorganization. However, the reorganization is particularly preferably carried out in the absence of a solvent.

The amount of cation exchange resin to be used, based on the reaction mixture, is preferably from 1 to 15% by weight, particularly preferably from 2 to 10% by weight, said cation exchange resin comprising water within the abovementioned limits.

The process according to the invention can be carried out batchwise or continuously.

It may be advantageous to separate off a portion having a desired boiling range from the reorganized product which is obtained as a reaction mixture of the reorganization according to the invention. The remaining residue of the reorganized product which does not have the desired boiling range can be used again as starting material (organosiloxanes) in the reorganization. Particularly preferably, in particular if the process is carried out continuously, a portion having a desired boiling range is separated off from the polysiloxane mixture obtained and the remainder which does not have the desired boiling range is used again as starting material (organosiloxanes) in the reorganization. This separation can be effected, for example, by a simple thermal separation (such as, for example, by simple distillation or by similar measures).

The reorganized products (dimethylsiloxane mixtures) obtained by the process according to the invention may contain, for example, low-boiling compounds, such as, for example, hexamethyldisiloxane, octamethyltrisiloxane, decamethyltetrasiloxane and dodecamethylpentasiloxane ($N_2$, $N_3$, $N_4$ and $N_5$) or cyclic compounds, such as $D_4$ and $D_5$, originating from the starting material composition. These compounds (=sum ($N_2$–$N_5$+$D_4$+$D_5$)) are present in the reorganized products preferably in proportions of 35 to 73% by mass. All these abovementioned low molecular weight siloxane compounds can remain in the reorganized product since as a rule they do not present problems for the subsequent foaming process or have little effect. If desired, these compounds can, however, be completely or partly separated off from the reorganized product. This separation, too, can be effected, for example, by a simple thermal separation (such as, for example, by stripping, the use of a thin-film evaporator or by similar measures). The siloxane compounds separated off can then serve again as starting materials for further reorganization reactions according to the invention.

Such a separation of portions from the reorganized product obtained according to the invention may be necessary in particular when parts of the reorganized product obtained prove to be troublesome for certain special applications.

For the use of dimethylsiloxane mixtures as a stabilizer in HR polyurethane foams in the automotive sector, it may be advantageous, for example from the point of view of avoiding fogging, to break off all low-boiling siloxane compounds having a chain length of $<N=6$ by a simple thermal separation from the reorganized product obtained by the process according to the invention.

If desired for particular applications in HR polyurethane foam, relatively high-boiling polydimethylsiloxanes can also be thermally separated off from the reorganized products according to the invention which can be used directly as a PU cold foam stabilizer. These relatively high-boiling polydimethylsiloxanes, too, can be recycled as starting material into the reorganization according to the invention.

By means of the process according to the invention, the polydimethylsiloxane compositions described below can be directly prepared.

The compositions according to the invention containing polydimethylsiloxanes of the formula (1)

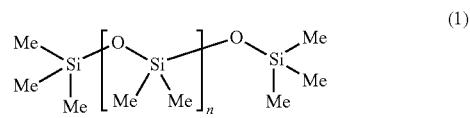

having a chain length $N=n+2$, the sum of the proportions of the polydimethylsiloxanes having the chain lengths $N=6$ and $N=7$ being ≥20% by weight, based on the total mass of the polydimethylsiloxanes, can be obtained by the above-described process according to the invention. A preferred composition which has a proportion of polydimethylsiloxanes with $N=6$ and $N=7$ of 20 to 35% by weight, based on the mass of the polydimethylsiloxanes, can be obtained directly as a reorganization product from the process according to the invention.

In the composition according to the invention, in particular the composition obtained directly as reorganized product, the proportion of the polydimethylsiloxanes of chain lengths $N=6$ to $N=12$ ($N_{6-12}$) is preferably ≥20% by weight, preferably from 20 to 58% by weight, and particularly preferably from 25 to 55% by weight, based on the mass of the polydimethylsiloxanes. The proportion of the polydimethylsiloxanes with $N≥13$ ($N_{≥13}$) in the composition according to the invention, in particular in the composition obtained directly as reorganized product, is preferably ≤7% by weight, preferably <6% by weight, particularly preferably <5% by weight and particularly preferably from 0.2 to 3% by weight, based on the mass of the polydimethylsiloxanes.

In the composition according to the invention, the sum of the linear polydimethylsiloxanes with $N<6$ ($N_2$ to $N_5$) and of the cyclic siloxanes having 4 or 5 silicon atoms ($D_4+D_5$) is preferably in the range of 35% by weight ≤Σ($N_2$, $N_3$, $N_4$, $N_5$, $D_4$, $D_5$)≤73% by weight, preferably in the range of 40% by weight ≤Σ($N_2$, $N_3$, $D_4$, $D_5$)≤70% by weight, based on the total mass of the polydimethylsiloxanes.

The compositions according to the invention, in particular the compositions obtained directly as reorganized products, preferably have 20 to 58% by weight of polydimethylsiloxanes having a chain length N of 6 to 12 ($N_{6-12}$), <7% by weight of polydimethylsiloxanes having a chain length N of ≥13 and 35 to 73% by weight of polysiloxanes having chain lengths of N=2 to 5 and cyclic siloxanes having 4 or 5 silicon atoms ($N_2$–$N_5$+$D_4$+$D_5$).

The compositions according to the invention, in particular the compositions obtained directly as reorganized products, preferably have 20 to 35% by weight of polydimethylsiloxanes having a chain length N of 6 and 7, 3 to 23% by weight of polydimethylsiloxanes having a chain length N of 8 to 12, ≤7% by weight of polydimethylsiloxanes having a chain length N of ≥13 and 35 to 73% by weight of polydimethylsiloxanes having chain lengths of N=2 to 5 and cyclic siloxanes having 4 or 5 silicon atoms.

The determination of the proportions of the polydimethylsiloxanes having the respective chain lengths can be effected, for example, by gas chromatography (GC) based on DIN 51 405. For example, the apparatus 5890 series II from Hewlett-Packard with thermal conductivity detector (TCD) can be used as the gas chromatograph for the measurement. A suitable separation column is, for example, a 1.8 m stainless steel column having an internal diameter of 2 mm, filled with 10% of UCW 98 on Chromosorb W HP 80 to 100 mesh. Suitable chromatographic separation conditions are, for example: carrier gas: 30 ml/min of helium, injection block temperature: 300° C., detector temperature (TCD): 300° C., temperature programme: 70 to 300° C. at 15° C./min, injection volume: 2 µl. The quantitative determination of the components is effected by the standard addition method. The standard chosen is $D_4$. The individual components are evaluated according to their signal area in relation to $D_4$ so that a result in % by weight, calculated as $D_4$ equivalent, (% by weight) is obtained.

The mass ratio Q of the polydimethylsiloxanes having N equal to 6 or 7 (sum $N_6$+$N_7$) to the polydimethylsiloxanes having N equal to 13 to 18 (sum $N_{13}$–$N_{18}$) in the composition according to the invention, in particular the composition obtained directly as a reorganization product mixture, is preferably 4 to 60, preferably 10 to 55.

Particularly preferred compositions according to the invention contain less than 1% by weight, of polydimethylsiloxanes of the formula (1) with N>18, preferably no polydimethylsiloxanes of the formula (1) with N>18. Such preferred compositions according to the invention can also be obtained, for example, by a simple distillation.

Another preferred composition according to the invention of polydimethylsiloxanes has a proportion of <5% by weight, preferably with zero proportion, of siloxane compounds, in particular linear and cyclic siloxane compounds, having boiling points below the boiling point of tetradecamethylhexasiloxane (N=6) (245° C. at atmospheric pressure). Such preferred compositions according to the invention can be obtained, for example, by separating off the polydimethylsiloxanes having a boiling point below the boiling point of tetradecamethylhexasiloxane (N=6) (245° C. at atmospheric pressure) from the reorganization mixture, for example by simple distillation.

A particularly preferred composition according to the invention contains less than 1% by weight, of polydimethylsiloxanes of the formula (1) with N>18, preferably no polydimethylsiloxanes, and less than 1% by weight of polydimethylsiloxanes of chain lengths N≥13 and preferably a proportion of less than 1% by weight, preferably zero proportion, of siloxane compounds $\Sigma(N_2, N_3, N_4, N_5, D_4, D_5)$, which have a lower boiling point than tetradecamethylhexasiloxane (N=6). Such preferred compositions can be obtained, starting from the reorganization product mixture, by removing the corresponding compounds, for example by a simple distillation.

The compositions according to the invention can be used as stabilizers, in particular cell-regulating stabilizers, in polyurethane foams, preferably polyurethane foams of the cold foam type. Compositions according to the invention which are obtained directly as reorganization product mixture are preferably used thereby.

As already described above, it is possible in particular according to the invention for the compositions which are obtainable by the process according to the invention to be used as stabilizers in polyurethane foams, preferably compositions used being those which are obtained directly as process products from the reorganization, i.e. without a further working-up step, in particular without a further separation step.

The compositions according to the invention or the compositions obtained according to the invention are particularly preferably used as a stabilizer in (high resilience) polyurethane foams (also referred to as cold foams or HR foams), which are used in means of transport, in particular in motor vehicles, such as, for example, cars, lorries or buses. In the case of this use, it may be advantageous to use a composition according to the invention which contains less than 1% by weight of compounds or preferably no compounds which have a boiling point which is lower than the boiling point of polydimethylsiloxanes of the formula (1) with N=6. By using these preferred compositions, emissions which are deposited in motor vehicles on the panes and may thus impair the vision can be avoided.

In the examples given below, the present invention is described by way of example without it being intended to limit the invention, the range of application of which is evident from the entire description and the claims, to the embodiments mentioned in the examples.

EXAMPLES

Determination of the proportions of the polydimethylsiloxanes having the respective chain lengths was carried out by gas chromatography (GC) based on DIN 51 405. A gas chromatograph of the type 5890 series II from Hewlett-Packard having a thermal conductivity detector (TCD) was used for the measurement. The separation column used was a 1.8 m stainless steel column having an internal diameter of 2 mm, filled with 10% of UCW 98 on Chromosorb W HP 80 to 100 mesh. The chromatographic separation conditions set were the following: carrier gas: 30 ml/min of helium, injection block temperature: 300° C., detector temperature (TCD): 300° C., temperature programme: 70 to 300° C. at 15° C./min, injection volume: 2 µl. The quantitative determination of the components was effected by the standard addition method. The standard chosen was $D_4$. The individual components were evaluated according to their signal area in relation to $D_4$ so that a result in % by weight, calculated as $D_4$ equivalent, (% by weight), was obtained.

Examples 1 to 10 and Comparative Examples 1 and 2

Preparation of the Polysiloxanes

The examples were carried out partly as individual experiments (Examples 8, 9 and 10) or as series of experiments (Examples 1 and 2, 3 and 4, 5 to 7 and Comparative Experiments 1a and 1b).

In a 1 l four-necked flask equipped with a KPG stirrer, reflux condenser and internal thermometer, the respective siloxane reactants (for example 228 g of hexamethyldisiloxane and 521 g of decamethylcyclopentasiloxane) were heated to the respective reaction temperature with stirring and then treated with the predried cation exchange resin Lewatit® K 2621 from Bayer AG (3% by mass, based on the total batch). After predetermined times, samples were taken from the reaction mixture once (individual experiment) or several times (series of experiments) with the aid of a syringe, upstream of which a syringe filter was connected, and said samples were transferred to a rolled-edge jar having a septum closure, sealed and then analyzed by gas chromatography. The syringe filter served both for preserving the originally used amount of catalyst in the reaction flask and for immediately stopping reorganization in the freshly taken sample.

The following is stated in Table 1 below: the water content of the cation exchange resin acting as a catalyst, the reaction temperature, the reaction time and the results of the analysis of the end products: the proportion of siloxanes having a chain length N=6 and N=7, the proportion of siloxanes having the chain lengths N=13 to N=18 and the proportion of siloxanes $D_4$, $D_5$, N=2 and N=3.

using sulphonic acid-containing cation exchange resins which have a higher water content. As shown by Comparative Example 2, in the case of a water content in the cation exchange resin which is too low, a composition which contains a high proportion of polydimethylsiloxanes with N=13 to 18 is obtained. By the use according to the invention of sulphonic acid-containing cation exchange resins having water contents of 8 to 25% by weight, preferably 10 to 20% by weight and particularly preferably 12 to 18% by weight, it is thus possible directly to obtain compositions which, as will be shown in the following examples, can be used directly as HR-PU stabilizers.

Examples 11 to 20

Distillative Purification of the Reorganization Products

In a 50 ml one-necked flask equipped with a magnetic stirring bar, Anschütz attachment and Claisen condenser, the respective siloxane mixtures were heated over an oil bath to an oil bath temperature of 215° C. with stirring. A pressure of 12 mbar or 1 mbar was applied thereby. The initially intro-

TABLE 1

Results of Examples 1 to 10 and of Comparative Examples 1 and 2

| Examples | $H_2O$ content of the catalyst/ % by wt. | Temp./ ° C. | Reaction time/min | Proportion of N6 + N7/ % by wt. | Proportion of N13 – N18/ % by wt. | Proportion of D4 + D5 + N2 + N3/ % by wt. |
|---|---|---|---|---|---|---|
| 1 | 15 | 40 | 25 | 24.5 | 0.7 | 60 |
| 2 | 15 | 40 | 45 | 28.3 | 2.0 | 43.1 |
| 3 | 12 | 30 | 30 | 25.3 | 0.7 | 60 |
| 4 | 12 | 30 | 50 | 29.2 | 2.0 | 45 |
| 5 | 20 | 30 | 50 | 21.9 | 0.4 | 67 |
| 6 | 20 | 30 | 80 | 27.4 | 0.8 | 56 |
| 7 | 20 | 30 | 130 | 30 | 1.9 | 45 |
| 8 | 10 | 50 | 30 | 30 | 3.1 | 33.2 |
| 9 | 10 | 50 | 20 | 21 | 2.7 | 63 |
| 10 | 20 | 50 | 40 | 25.4 | 5.4 | 29.3 |
| Comp. 1a | 50 | 30 | 50 | 0.5 | 0 | 99 |
| Comp. 1b | 50 | 30 | 180 | 0.7 | 0 | 99 |
| Comp. 2 | 5 | 40 | 180 | 16.7 | 11.7 | 24.2 |

As can be seen from Table 1, the reorganization compositions which were obtained according to the invention have a substantially higher proportion of polydimethylsiloxanes with N=6+7 than those compositions which were obtained duced mixture was cooled with ice water in order to condense the distillate as completely as possible. The distillates and residues obtained were analyzed as described above by gas chromatography. The results are listed in Table 2.

TABLE 2

Results of Examples 11 to 20

| Example | Siloxane mixture from Example | Bottom product/ distillate | Pressure/ mbar | Proportion of N6 + N7/ % by wt. | Proportion of N13 – N18/ % by wt. | Proportion of D4 + D5 + N2 + N3/ % by wt. |
|---|---|---|---|---|---|---|
| 11 | 2 | Distillate | 12 | 26.9 | 1.9 | 45.6 |
| 12 | 2 | Bottom product | 12 | 17.3 | 19.8 | 0.1 |
| 13 | 10 | Distillate | 12 | 27.6 | 0.1 | 41.4 |
| 14 | 10 | Bottom product | 12 | 15.5 | 20.1 | 0.1 |
| 15 | 8 | Distillate | 12 | 31.2 | 0.1 | 43.6 |
| 16 | 8 | Bottom product | 12 | 14.1 | 18.0 | 0 |
| 17 | 9 | Distillate | 12 | 18.0 | 0 | 71.9 |
| 18 | 9 | Bottom product | 12 | 18.2 | 20.3 | 0.1 |

TABLE 2-continued

Results of Examples 11 to 20

| Example | Siloxane mixture from Example | Bottom product/ distillate | Pressure/ mbar | Proportion of N6 + N7/ % by wt. | Proportion of N13 – N18/ % by wt. | Proportion of D4 + D5 + N2 + N3/ % by wt. |
|---|---|---|---|---|---|---|
| 19 | 8 | Distillate | 1 | 49.9 | 0.1 | 9.7 |
| 20 | 10 | Distillate | 1 | 39.2 | 0.2 | 13.3 |

Examples 21 to 48

Preparation of the Flexible Polyurethane Cold Foams

Formulations Used:
Formulation A:
90 parts of polyol having an OH number of 32 mg KOH/g and a molar mass of 5500 g/mol, 10 parts of a polymer polyol (43% of SAN) having an OH number of 20 mg KOH/g and a molar mass of 5000 g/mol, 1.2 parts of stabilizer consisting of a 10% strength solution of the corresponding siloxane in a butanol-initiated polypropylene glycol having a molar mass of 400, 4 parts of water, 0.9 part of diethanolamine, 0.4 part of TEGOAMIN® MS 40 (Goldschmidt GmbH), 0.06 part of TEGOAMIN® BDE (Goldschmidt GmbH), 0.6 part of glycerol and 46 parts of isocyanate (T80=2,4- and 2,6-toluylene diisocyanate isomer mixture in the ratio 80:20).

Formulation B:
73 parts of polyol having an OH number of 32 mg KOH/g and a molar mass of 5500 g/mol, 27 parts of a polymer polyol (43% of SAN) having an OH number of 20 mg KOH/g and a molar mass of 5000 g/mol, 1.5 parts of stabilizer consisting of a 10% strength solution of the corresponding siloxane in a butanol-initiated polypropylene glycol having a molar mass of 400, 4 parts of water, 0.9 part of diethanolamine, 0.4 part of TEGOAMIN® 33 (Goldschmidt GmbH), 0.06 part of TEGOAMIN® BDE (Goldschmidt GmbH), 0.6 part of glycerol and 46 parts of isocyanate (T80=2,4- and 2,6-toluylene diisocyanate isomer mixture in the ratio 80:20).

Formulation C:
70 parts of polyol (Voranol® HF 505 from Dow) having an OH number of 29 mg KOH/g and a molar mass of about 6000 g/mol, 30 parts of a polymer polyol (Voralux® HL 400) (43% of SAN) having an OH number of 33 mg KOH/g and a molar mass of 3000 g/mol, 0.8 part of stabilizer consisting of a 10% strength solution of the corresponding siloxane in a butanol-initiated polypropylene glycol having a molar mass of 400, 4.5 parts of water, 1.75 parts of diethanolamine, 0.12 part of TEGOAMIN® ZE 1 (Goldschmidt GmbH), 0.08 part of TEGOAMIN® BDE (Goldschmidt GmbH), 0.12 part of Kosmos® 29 and 1.2 parts of Voranol® CP 1421 (from Dow) and 53 parts of isocyanate (T80=2,4- and 2,6-toluylene diisocyanate isomer mixture in the ratio 80:20).

Formulation D:
100 parts of polyol having an OH number of 35 mg KOH/g and a molar mass of 5000 g/mol, 0.6 part of stabilizer in Examples 43 and 45 and 0.3 part in Examples 44, 46, 47 and 48, the stabilizer consisting of a 10% strength solution of the corresponding siloxane in a butanol-initiated polypropylene glycol having a molar mass of 400, 3 parts of water, 2 parts of triethanolamine, 0.6 part of TEGOAMIN® 33 (Goldschmidt GmbH) and 0.2 part of diethanolamine and a mixture of 18.5 parts of polymeric MDI (44V20 from Bayer) and 27.7 parts of TDI (T80).

Examples 21 to 25

Preparation of Moulded Foam Using Formulation A

The foams were prepared in a known manner by mixing all components, except for the isocyanate, in a beaker, then adding the isocyanate and stirring it in rapidly at a high stirrer speed. The reaction mixture was then introduced into an industrially used mould for an automobile seat, which mould was heated to a temperature of 65° C., and the material was allowed to cure for 6 minutes. Thereafter, the compressibility (CO) of the foam was rated with values from 1 to 10, the value 1 representing a very open-cell foam and the value 10 a very closed-cell foam. In addition, the flow (FL) of the foaming material was rated with values from 1 to 5, 1 representing very good flow and 5 very poor flow. These effects are displayed particularly at constrictions in the mould. Thereafter, the foams were cut open in order to assess the quality (skin and edge zone) and to determine the cell count (CC). In Table 3 below, the results of Examples 21 to 25 are summarized. The assessments and the siloxane used in each case are mentioned. From the point of view of the evaluation of the performance characteristics, all HR-PU foams mentioned here are good and technically usable.

TABLE 3

Results for Examples 21 to 25 using the formulation A

| Example | CO | FL | CC | Skin | Edge zone | Siloxane from example |
|---|---|---|---|---|---|---|
| 21 | 2 | 2 | 11 | Good | Good | 4 |
| 22 | 2 | 2-3 | 11 | Very good | Very good | 3 |
| 23 | 1 | 1 | 10 | Good | Very good | 5 |
| 24 | 1 | 1 | 10 | Good | Good | 6 |
| 25 | 1-2 | 2 | 11 | Good | Good | 7 |

Examples 26 to 33

Preparation of Slabstock Foam Using Formulation C

The foams were prepared in a known manner by mixing all components, except for the isocyanate, in a beaker, then adding the isocyanate and stirring it in rapidly at a high stirrer speed. Thereafter, the reaction mixture was introduced into a container lined with paper and having a base area of 28×28 cm. The height of rise (HR in cm) and the settling (SE in cm) were determined. The blow-off (BO) of the foam was rated with values from 0 to 3, 0 being allocated for poor or undetectable blow-off and 3 for very strong blow-off, values of 1 to 2 being desirable. Settling is designated as the decrease in the height of rise in cm within one minute after reaching the maximum height of rise. Blow-off is designated as the escape of the blowing gases from the opened cells of the foam.

After curing of the foam, it was cut open and the cell count (CC in cm-1) was determined, and the quality of the foam (cell size distribution, edge zones) was generally assessed. In Table 4 below, the results of Examples 26 to 33 are summarized. The assessments and the siloxane used in each case are shown.

TABLE 4

Results for Examples 26 to 33 using formulation C

| Example | HR | SE | BO | CC | Quality | Siloxane from Example |
|---|---|---|---|---|---|---|
| 26 | 26.5 | 0.2 | 2 | 8 | Good | 12 |
| 27 | 26.8 | 0.6 | 1-2 | 9 | Good | 11 |
| 28 | 26.2 | 2.1 | 1 | 9 | Good (moderate) | 15 |
| 29 | 27.8 | 0.2 | 1 | 7 | Good (moderate) | 18 |
| 30 | 25.9 | 1.7 | 1 | 8 | Good | 17 |
| 31 | 27.0 | 0.1 | 2 | 9 | Good | 14 |
| 32 | 26.3 | 1.9 | 1 | 8 | Good (moderate) | 13 |
| 33 | 26.8 | 0.2 | 1 | 9 | Good | 10 |

Examples 34 to 48

Preparation of Moulded Foam Using Formulations B and D

The foams were prepared in a known manner by mixing all components, except for the isocyanate, in a beaker, then adding the isocyanate and stirring it in rapidly at a high stirrer speed. Thereafter, the reaction mixture was introduced into a cuboid mould having the dimensions 40×40×10 cm which had been heated to a temperature of 40° C. in the case of formulation D and to a temperature of 65° C. in the case of formulation B, and the material was allowed to cure for 6 minutes in the case of formulation B and for 10 minutes in the case of formulation D.

Thereafter, the compression forces were measured. The foams were compressed thereby 10 times to 50% of their height. Here, the 1st measured value (CO 1 in Newton) is a measure of the open-cell character of the foam. Thereafter, complete (manual) compression (opening of the compressible closed cells) was effected in order to be able to determine the hardness of the compressed foam in the case of the 11th measured value (CO 11 in Newton). Thereafter, the foams were cut open in order to assess skin and edge zone and to determine the cell count (CC). In Table 5 below, the results of Examples 34 to 48 are summarized. The assessments, the formulation (F) used and the siloxane used in each case are shown.

TABLE 5

Results for Examples 34 to 48 using formulations B or D

| Example | F | CO 1 | CO 11 | CC | Skin | Edge zone | Siloxane from example |
|---|---|---|---|---|---|---|---|
| 34 | B | 1754 | 185 | 11 | Good | Good | 9 |
| 35 | B | 1889 | 162 | 11 | Good | Good | 10 |
| 36 | B | 1827 | 173 | 12 | Good | Good | 2 |
| 37 | B | 1772 | 170 | 12 | Good | Good | 2 |
| 38 | B | 1887 | 163 | 12 | Good | Good | 5 |
| 39 | B | 1831 | 166 | 12 | Good | Good | 6 |
| 40 | B | 1784 | 165 | 12 | Good | Good | 7 |
| 41 | B | 1550 | 155 | 12 | Good | Good | 19 |
| 42 | B | 1701 | 149 | 12 | Good | Good | 20 |
| 43 | D | 1616 | 150 | 11 | Good | Good | 1 |
| 44 | D | 1213 | 132 | 10 | Good | Good | 13 |
| 45 | D | 1002 | 111 | 11 | Good | Good | 13 |
| 46 | D | 1405 | 132 | 10 | Good | Good | 3 |
| 47 | D | 1304 | 131 | 11 | Good | Good | 19 |
| 48 | D | 1351 | 129 | 11 | Good | Good | 20 |

It was possible to show that both the undistilled and the distilled reorganization compositions which were prepared by the process according to the invention are suitable as an additive (stabilizer, cell regulator) in HR-PU foam.

The invention claimed is:

1. A composition containing different polydimethylsiloxanes of formula (1)

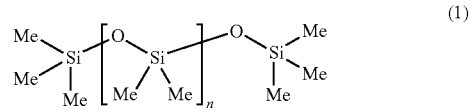

having a chain length N=n+2, wherein the sum of polydimethylsiloxanes with N=6 and N=7 is ≥20% by weight, and the sum of polydimethylsiloxanes having a boiling point lower than the boiling point of a polydimethylsiloxane with N=6 is less than 5% by weight, wherein said % by weight is based on the mass of the polydimethylsiloxanes of formula (1).

2. The composition according to claim 1, wherein the sum of polydimethylsiloxanes with N=6 to N=12 is 20 to 58% by weight, based on the mass of the polydimethylsiloxanes of formula (1).

3. The composition according to claim 1, wherein the sum of polydimethylsiloxanes with N≥13 is <7% by weight, based on the mass of the polydimethylsiloxanes of formula (1).

4. The composition according to claim 1, wherein the composition contains 20 to 58% by weight of polydimethylsiloxanes having a chain length N of 6 to 12, and 7% by weight of polydimethylsiloxanes having a chain length N of ≥13.

5. The composition according to claim 1, wherein the composition contains 20 to 35% by weight of polydimethylsiloxanes having a chain length N of 6 and 7, 3 to 23% by weight of polydimethylsiloxanes having a chain length N of 8 to 12, and ≤7% by weight of polydimethylsiloxanes having a chain length N of ≥13.

6. The composition according to claim 1, wherein a mass ratio Q of the polydimethylsiloxane with N=6 or 7 to the polydimethylsiloxane with N=13 to 18 is from 4 to 60.

7. The composition according to claim 1, wherein the composition contains less than 1% by weight of compounds having a boiling point lower than the boiling point of a polydimethylsiloxane of the formula (1) with N=6, wherein said % by weight is based on the mass of the polydimethylsiloxanes of formula (1).

8. A method of forming a polyurethane foam comprising adding a composition according to claim 1 to a reaction mixture comprising polyurethane foam reactants.

* * * * *